United States Patent [19]

Carney et al.

[11] 4,272,626
[45] Jun. 9, 1981

[54] METHOD OF PRODUCING 1-EPI-2-DEOXYFORTIMICIN A AND INTERMEDIATES THEREFOR

[75] Inventors: Ronald E. Carney, Gurnee; James B. McAlpine, Libertyville, both of Ill.

[73] Assignee: Abbott Laboratories, North Chicago, Ill.

[21] Appl. No.: 79,018

[22] Filed: Sep. 26, 1979

[51] Int. Cl.$^3$ ............................................. C07H 15/22
[52] U.S. Cl. ................................... 536/17 R; 424/180
[58] Field of Search ...................................... 536/17 R

[56] References Cited

U.S. PATENT DOCUMENTS

| | | | |
|---|---|---|---|
| 4,000,261 | 12/1976 | Daniels | 536/17 |
| 4,078,139 | 3/1978 | Barton et al. | 536/17 |
| 4,085,208 | 4/1978 | Mallams et al. | 536/17 |
| 4,176,178 | 11/1979 | Martin et al. | 536/17 |

*Primary Examiner*—Johnnie R. Brown
*Attorney, Agent, or Firm*—Robert L. Niblack; Gildo E. Fato; Joyce R. Niblack

[57] ABSTRACT

A method of producing 1-epi-2-deoxyfortimicin A, key intermediates therefor and an improved process for synthesizing the key intermediate 1,2-di-epi-fortimicin A.

4 Claims, No Drawings

METHOD OF PRODUCING 1-EPI-2-DEOXYFORTIMICIN A AND INTERMEDIATES THEREFOR

BACKGROUND OF THE INVENTION

The antibiotic 1-epi-2-deoxyfortimicin A has been reported to have been produced by fermentation of a suitable Saccharopolyspora species (See Derwent DT2813-021).

The present invention provides a novel method of making 1-epi-2-deoxyfortimicin A.

SUMMARY OF THE DISCLOSURE 1-epi-2-Deoxyfortimicin A is prepared from fortimicin A by reducing 1-epi-2-deoxy-2-oxo-tetra-N-benzyloxycarbonylfortimicin A with sodium borohydride, treating the resulting 1,2-di-epi-tetra-N-benzyloxycarbonylfortimicin A with thiocarbonylimidazole to obtain the corresponding 2-thiocarbonylimidazole, treating the latter intermediate with tri-n-butylstannane to obtain 1-epi-2-deoxy-tetra-N-benzyloxycarbonylfortimicin A and deprotecting the latter to obtain the desired product which heretofore has been obtainable only by fermentation.

DETAILED DESCRIPTION

1-Epi-2-deoxyfortimicin A is represented by the formula:

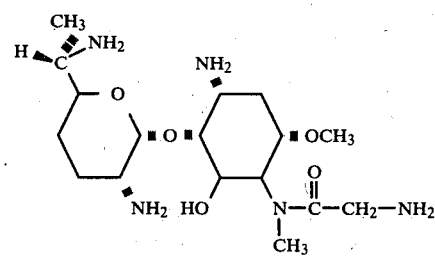

1-epi-2-Deoxyfortimicin A has heretofore been prepared by fermentation. Prior attempts to simply deoxygenate 1-epi-fortimicin A have resulted in 1-epi-5-deoxyfortimicin fortimicin A rather than the desired 1-epi-2-deoxyfortimicin A.

Generally speaking, according to the process of the present invention, 1-epi-2-deoxyfortimicin A is prepared from fortimicin A by reducing 1-epi-2-deoxy-2-oxo-tetra-N-benzyloxyfortimicin A with sodium borohydride in an inert, relatively non-polar organic solvent such as chloroform, methylene chloride, dioxane, etc. Treatment of the resulting 1, 2-di-epi-tetra-N-benzyloxycarbonyl-fortimicin A with a suitable agent which will produce a thiocarbonate, such as thiocarbonylimidazole, in a suitable organic solvent such as ethyl acetate, dioxane, toluene, etc., yields the corresponding 2-thiocarbonylimidazole intermediate. Treatment of the latter with tri-n-butylstannane in a suitable organic solvent provides 1-epi-2-deoxy-tetra-N-benzyloxycarbonylfortimicin A. Deprotection of the latter in an acid medium in the presence of a suitable acid to provide the desired salt results in a 1-epi-2-deoxyfortimicin A salt.

1-epi-2-Deoxyfortimicin A is also known as spororacin.

The present invention also provides an improved process for preparing the key intermediate, 1,2-di-epifortimicin A, which heretofore has been prepared in a process involving substantially more steps as disclosed in commonly assigned, co-pending U.S. patent application Ser. No. 079,135, filed of even date herewith.

The following examples set forth the method of this invention:

EXAMPLE 1

1-epi-2-Deoxy-2-oxo-tetra-N-benzyloxycarbonylfortimicin A

A solution of tetra-N-benzyloxycarbonylfortimicin A (5.0 g, 5.3 millimole) in acetone (100 ml) is treated at 4° C. with Jones Reagent (aqueous chromic acid in acetone), (4.0 ml). The mixture is maintained at 4° C. for 35 minutes and poured into water (7 volumes). The products are extracted with methylene chloride and the solution dried over magnesium sulfate. Solvent is removed and the residue is chromatographed over a column of silica get to give 1-epi-2-deoxy-2-oxo-tetra-N-benzyloxycarbonylfortimicin A (1.81 g).

Analysis calcd. for $C_{49}H_{57}N_5O_{14}$: C, 62.61; H, 6.11; N, 7.45. Found: C, 62.74; H, 6.03; N, 7.43.

EXAMPLE 2

1,2-Di-epi-tetra-N-benzyloxycarbonylfortimicin A

1-Epi-2-deoxy-2-oxo-tetra-N-benzyloxycarbonylfortimicin A (25 g, 26.5 millimole) is dissolved in chloroform (400 ml) and treated with sodium borohydride (400 mg) at room temperature. The mixture is stirred for 72 hours. The excess borohydride is consumed by the addition of acetone and the mixture is evaporated to dryness under reduced pressure.

The residue is dissolved in a minimum volume of dichloroethane methanol [24:1(v/v)] and chromatographed over a column of silica gel (7 cm×70 cm) packed in the same solvent system to afford 1.8 g of the desired product. PMR $(CDCl_3)\delta$ 1.01 d($C_6$, —$CH_3$)(J=6.7Hz), 2.88 s (N$CH_3$). 3.46 s(O$CH_3$). The CMR spectrum is set forth in the table following the Examples.

EXAMPLE 3

1-epi-Tetra-N-benzyloxycarbonylfortimicin A-2-epi-thiocarbonylimidazolide 1,2-epi-Tetra-N-benzyloxycarbonylfortimicin A (300 mg. 0.318 millimole) is dissolved in ethyl acetate (15 ml) and treated with N,N'-thiocarbonyldiimidazole (200 mg) under reflux for 6½ hours. Solvent is removed under reduced pressure. The residue is dissolved in a minimum volume of dichloroethane-ethanol [24:1(v/v)] and chromatographed over a column of silica gel (1.8 cm×50 cm) to yield 70 mg of the desired product. PMR $(CDCl_3)\delta$ 1.11 d($C_6$, —$CH_3$)(J=7.0 Hz), 2.96 s (N$CH_3$), 3.28 s(O$CH_3$). The CMR spectrum is set forth in the table following the Examples.

EXAMPLE 4

1-epi-2-Deoxy-tetra-N-benzyloxycarbonylfortimicin A 1-epi-Tetra-N-benzyloxycarbonylfortimicin A-2-epi-thiocarbonylimidazolide (70 mg) is dissolved in dioxane (15 ml) and the solution is added dropwise to a solution of tri-n-butylstannane (0.15 ml) in dioxane (12 ml) and heated under reflux in an atmosphere of nitrogen for 2 hours. The reaction mixture is evaporated to dryness under reduced pressure. The residue is dissolved in a minimum volume of ethyl acetate and chromatographed over a column of silica gel (1.8 cm×65 cm) to afford 40 mg of product. PMR(CDCl$_3$) δ 1.06 d(C$_6$, —CH$_3$)(J=6.3 Hz), 2.89 s(NCH$_3$), 3.31 s(OCH$_3$). The CMR spectrum is set forth in the table following the examples.

EXAMPLE 5

1-epi-2-Deoxyfortimicin A tetrahydrochloride 1-epi-2-Deoxy-tetra-N-benzyloxycarbonylfortimicin A (40 mg) is dissolved in 0.2 M methanolic hydrogen chloride and hydrogenolyzed over 5% palladium on carbon (40 mg) at 3 atmospheres of pressure for 4 hours. The catalyst is removed by filtration and the filtrate evaporated to dryness under reduced pressure to give 28 mg of product. Mass spectrum M+1 peak for free base m/e 390.2725 calc. for C$_{17}$H$_{36}$N$_5$O$_5$ M=390.2717. PMR (D$_2$O) δ (uncorrected from external tetramethylsilane) 1.36 d (C$_6$, —CH$_3$)(J=7 Hz), 3.11 s (NCH$_3$), 3.46 s (OCH$_3$).

EXAMPLE 6

1,2-Di-epi-fortimicin A tetrahydrochloride 1,2-Di-epi-tetra-N-benzyloxycarbonylfortimicin A (400 mg) in 0.2 M methanolic hydrogen chloride (150 ml) was shaken under 3 atmospheres of hydrogen in the presence of 5% palladium on carbon (250 mg) for 4 hours. The mixture was filtered and solvent was removed from the filtrate under reduced pressure to yield 1,2-di-epi-fortimicin A tetrahydrochloride (300 mg) Mass spectrum M+ (for free base) m/e 405.2588 calculated for C$_{17}$H$_{35}$N$_5$O$_6$ M=405.2587 CMR as shown in table.

TABLE

| | Example 2 (CDCl$_3$) | Example 3 (CDCl$_3$) | Example 5 (D$_2$O) | Example 6 (D$_2$O) |
| --- | --- | --- | --- | --- |
| C-1' | 100.4 | 101.1 | 92.6 | 92.8 |
| C-2' | 50.3 | 50.4 | 49.6 | 51.9 |
| C-3' | 23.6 | 23.4 | 21.2 | 21.1 |
| C-4' | 26.3 | 27.4 | 26.2 | 26.3 |
| C-5' | 71.0 | 71.1 | 70.9 | 70.9 |
| C-6' | 49.5 | 49.7 | 47.3 | 49.6 |
| C—CH$_3$ | 17.4 | 18.9 | 15.2 | 15.2 |
| C-1 | 61.1 | 67.4 | 51.8 | 60.4 |
| C-2 | 70.6 | 83.6 | 29.2 | 71.8 |
| C-3 | 82.7 | 82.4 | 71.8 | 78.0 |
| C-4 | 53.3 | 51.6 | 56.5 | 53.0 |
| C-5 | 68.4 | 72.2 | 67.9 | 67.8 |
| C-6 | 74.7 | 74.9 | 73.3 | 73.1 |
| CH$_3$ | 58.7 | 57.8 | 56.5 | 54.5 |
| NCH$_3$ | 32.1 | 32.3 | 32.0 | 32.3 |
| GlyCH$_2$ | 43.1 | 43.2 | 41.3 | 41.3 |
| GlyCO | 169.6 | 169.9 | — | 168.9 |

Assignments have been made by analogy with like carbon in other fortimicin derivatives and from known effects of structures on CMR chemical shifts. Interchanges between assignments to Cs of resonances of similar chemical shifts does not affect characterization or structural inferences drawn.

We claim:
1. 1-epi-Tetra-N-benzyloxycarbonylfortimicin A-2-epi-thiocarbonylimidazolide.
2. A process for producing 1-epi-2-deoxyfortimicin A comprising the steps of: (a) reducing 1-epi-2-deoxy-2-oxo-tetra-N-benzyloxycarbonyl A with sodium borohydride to obtain 1,2-di-epi-tetra-N-benzyloxycarbonylfortimicin A; (b) reacting said 1,2-di-epi-tetra-N-benzyloxycarbonylfortimicin A with N,N-thiocarbonyldiimidazole; treating the resulting 2-thiocarbonylimidazole intermediate with tri-n-butylstannane; (d) hydrogenating said intermediate to remove the N-benzyloxycarbonyl protecting groups; (e) and isolating said 1-epi-2-deoxyfortimicin A.
3. An improved process for producing 1,2-di-epi-fortimicin A comprising the steps of: treating 1-epi-2-deoxy-2-oxo-tetra-N-benzyloxycarbonylfortimicin A with sodium borohydride to obtain 1,2-di-epi-tetra-N-benzyloxycarbonylfortimicin A; hydrogenating said intermediate to remove the N-benzyloxycarbonyl protecting groups; and isolating said 1,2-di-epi-fortimicin A.
4. 1-epi-2-Deoxy-tetra-N-benzyloxycarbonylfortimicin A.

* * * * *